(12) United States Patent
Zoabi et al.

(10) Patent No.: US 11,103,249 B2
(45) Date of Patent: *Aug. 31, 2021

(54) BALLOON POSITIONING IN A SINUPLASTY PROCEDURE

(71) Applicant: Biosense Webster (Israel) Ltd., Yokneam (IL)

(72) Inventors: Akram Zoabi, Kfar Masser (IL); Fady Massarwi, Baka Al Gharbiyya (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 306 days.

This patent is subject to a terminal disclaimer.

(21) Appl. No.: 16/400,272

(22) Filed: May 1, 2019

(65) Prior Publication Data

US 2019/0314032 A1   Oct. 17, 2019

Related U.S. Application Data

(63) Continuation of application No. 15/228,607, filed on Aug. 4, 2016, now Pat. No. 10,321,913.

(51) Int. Cl.
*A61B 17/12* (2006.01)
*A61B 17/24* (2006.01)
(Continued)

(52) U.S. Cl.
CPC ........ *A61B 17/12104* (2013.01); *A61B 5/066* (2013.01); *A61B 5/1076* (2013.01);
(Continued)

(58) Field of Classification Search
CPC .......... A61B 17/1204; A61B 17/12104; A61B 17/12136; A61M 25/10; A61M 25/0662;
(Continued)

(56) References Cited

U.S. PATENT DOCUMENTS

| 5,391,199 A | 2/1995 | Ben-Haim et al. |
| 6,239,724 B1 | 5/2001 | Doron et al. |

(Continued)

FOREIGN PATENT DOCUMENTS

| CN | 202505930 U | 10/2012 |
| CN | 103118584 A | 5/2013 |

(Continued)

OTHER PUBLICATIONS

Chinese Office Action and Search Report dated Dec. 30, 2020 for Application No. 201710664628.5, 7 pages.

(Continued)

*Primary Examiner* — Katrina M Stransky
(74) *Attorney, Agent, or Firm* — Frost Brown Todd LLC

(57) ABSTRACT

A method includes inserting into a patient organ a catheter including a position sensor, a device and a handle. The position sensor is attached to a distal end of the catheter. The device is movable along the catheter. The handle includes a control for navigating the device along the catheter to a target location in the patient organ. Based on a location of the position sensor, a target position of the control on the handle that corresponds to the target location of the device is estimated. A marker is set to mark the target position of the control on the handle, and the device is navigated to the target location by setting the control to the marker.

20 Claims, 3 Drawing Sheets

(51) Int. Cl.
- *A61M 25/10* (2013.01)
- *A61M 25/01* (2006.01)
- *A61M 25/00* (2006.01)
- *A61B 5/00* (2006.01)
- *A61B 5/06* (2006.01)
- *A61B 5/107* (2006.01)
- *A61B 34/20* (2016.01)
- *A61B 90/00* (2016.01)

(52) U.S. Cl.
CPC ........ *A61B 5/6851* (2013.01); *A61B 17/1204* (2013.01); *A61B 17/12136* (2013.01); *A61B 17/24* (2013.01); *A61B 34/20* (2016.02); *A61M 25/10* (2013.01); *A61B 5/062* (2013.01); *A61B 5/6853* (2013.01); *A61B 2034/2051* (2016.02); *A61B 2090/0811* (2016.02); *A61B 2505/05* (2013.01); *A61B 2562/0223* (2013.01); *A61B 2576/02* (2013.01); *A61M 25/0113* (2013.01); *A61M 2025/0008* (2013.01); *A61M 2025/0166* (2013.01)

(58) Field of Classification Search
CPC .. A61M 2025/0687; A61M 2210/0681; A61M 2210/0618
See application file for complete search history.

(56) References Cited

U.S. PATENT DOCUMENTS

| | | | |
|---|---|---|---|
| 6,332,089 B1 | 12/2001 | Acker et al. | |
| 6,484,118 B1 | 11/2002 | Govari | |
| 6,618,612 B1 | 9/2003 | Acker et al. | |
| 6,690,963 B2 | 2/2004 | Ben-Haim et al. | |
| 10,321,913 B2 | 6/2019 | Zoabi et al. | |
| 2002/0065455 A1 | 5/2002 | Ben-Haim et al. | |
| 2003/0120150 A1 | 6/2003 | Govan | |
| 2004/0068178 A1 | 4/2004 | Govan | |
| 2005/0131403 A1 | 6/2005 | Chang | |
| 2006/0095066 A1 | 5/2006 | Chang et al. | |
| 2006/0210605 A1 | 9/2006 | Chang et al. | |
| 2007/0129751 A1 | 6/2007 | Muni et al. | |
| 2007/0208252 A1* | 9/2007 | Makower | A61B 6/037 600/424 |
| 2009/0187222 A1 | 7/2009 | Barker | |
| 2010/0145340 A1 | 6/2010 | Phan et al. | |
| 2010/0312101 A1 | 12/2010 | Drontle et al. | |
| 2011/0004057 A1 | 1/2011 | Goldfarb et al. | |
| 2011/0028784 A1 | 2/2011 | Patil et al. | |
| 2012/0071727 A1 | 3/2012 | Hanson et al. | |
| 2012/0078377 A1 | 3/2012 | Gonzales et al. | |
| 2012/0259217 A1 | 10/2012 | Gerrans et al. | |
| 2013/0072958 A1 | 3/2013 | Ressemann et al. | |
| 2013/0184683 A1 | 7/2013 | Chow et al. | |
| 2014/0018732 A1* | 1/2014 | Bagaoisan | A61M 25/0147 604/95.04 |
| 2014/0107427 A1 | 4/2014 | Chow et al. | |
| 2014/0200444 A1 | 7/2014 | Kim et al. | |
| 2014/0343457 A1 | 11/2014 | Shekalim et al. | |
| 2015/0141819 A1 | 5/2015 | Linden et al. | |
| 2015/0250434 A1 | 9/2015 | Hall et al. | |
| 2016/0082233 A1 | 3/2016 | Ha et al. | |
| 2016/0287055 A1 | 10/2016 | Kesten et al. | |

FOREIGN PATENT DOCUMENTS

| | | |
|---|---|---|
| CN | 103124531 A | 5/2013 |
| CN | 103845053 A | 6/2014 |
| CN | 104619273 A | 5/2015 |
| CN | 105163677 A | 12/2015 |
| CN | 204932313 U | 1/2016 |
| EP | 1832307 A1 | 9/2007 |
| EP | 2508118 A1 | 10/2012 |
| EP | 2512359 A1 | 10/2012 |
| EP | 2662041 A2 | 11/2013 |
| WO | WO 1996/005768 A1 | 2/1996 |

OTHER PUBLICATIONS

European Search Report and Written Opinion dated Dec. 20, 2017 for EP Application No. 17184740, 8 pages.
Japanese Notification of Reasons for Refusal dated Jun. 28, 2021, for Application No. 2017-150464, 4 pages.

* cited by examiner

BALLOON POSITIONING IN A SINUPLASTY PROCEDURE

This application is a continuation of U.S. patent application Ser. No. 15/228,607, entitled "Balloon Positioning in a Sinuplasty Procedure," filed Aug. 4, 2016, now issued as U.S. Pat. No. 10,321,913 on Jun. 18, 2019.

FIELD OF THE INVENTION

The present invention relates generally to invasive medical devices, and particularly to methods and systems for balloon positioning in sinuplasty procedures.

BACKGROUND OF THE INVENTION

Catheters comprising an inflatable balloon may be used in various medical applications, such as sinuplasty.

For example, U.S. Patent Application Publication No. 2014/0107427, now U.S. Pat. No. 9,579,448, issued Feb. 28, 2017, whose disclosure is incorporated herein by reference, describes a medical device for the treatment and irrigation of a sinus opening. The device allows for single-handed operation to access, dilate and irrigate a sinus opening. The device includes a sinus guide 15 catheter, a guiding element, a balloon dilation catheter, a balloon catheter movement mechanism and a guiding element movement mechanism. A method for treating a sinus opening and irrigating a sinus is also described.

U.S. Patent Application Publication No. 2013/0184683, now U.S. Pat. No. 9,095,646, issued on Aug. 4, 2015, whose disclosure is incorporated herein by reference, describes a medical device for the treatment of a sinus opening. The medical device comprises a proximal end, a distal end, and a shaft system having an inflation lumen and an irrigation lumen the proximal and. The shaft system has a proximal shaft section and a distal shaft section. An inflatable balloon is attached to the distal shaft section in a position that is proximal to said distal end.

U.S. Patent Application Publication No. 2012/0259217, now U.S. Pat. No. 9,238,126, issued on Jan. 19, 2016, whose disclosure is incorporated herein by reference, describes a method of dilating a paranasal sinus ostium of a patient. The method includes inserting a catheter having at least one balloon into a sinus ostium having an ostial wall, inflating the balloon by supplying fluid thereto such that the balloon exerts a force on the ostial wall, determining at least one parameter of the balloon, establishing an amount the balloon can be inflated without fracturing the sinus ostium based at least in part on the determined parameter of the balloon, and dilating the sinus ostium by inflating the balloon to an amount that does not exceed the established amount.

SUMMARY OF THE INVENTION

An embodiment of the present invention that is described herein provides a method including inserting into a patient organ a catheter including a position sensor, a device and a handle. The position sensor is attached to a distal end of the catheter. The device is movable along the catheter. The handle includes a control for navigating the device along the catheter to a target location in the patient organ. Based on a location of the position sensor, a target position of the control on the handle that corresponds to the target location of the device is estimated. A marker is set to mark the target position of the control on the handle, and the device is navigated to the target location by setting the control to the marker.

In some embodiments, the method includes acquiring an anatomical image of the organ before inserting the catheter, and registering the location of the position sensor with the anatomical image. In other embodiments, allowed boundaries for the target location relative to the anatomical image are determined, and the target position is estimated based on the location of the position sensor on the anatomical image, the allowed boundaries, and predefined dimensions of the device. In yet other embodiments, the marker includes an adjustable mechanical stopper. A position of the mechanical stopper is adjusted to the target position on the handle, and the control is slid until hitting the stopper.

In an embodiment, the device includes an anchoring device for anchoring the distal end of the catheter in the body of the patient. In another embodiment, the anchoring device includes an inflatable balloon.

There is additionally provided, in accordance with an embodiment of the present invention, a system including a catheter and a processor. The catheter includes an insertion tube for insertion into a patient organ, a position sensor, a device and a handle. The position sensor is attached to a distal end of the catheter and is configured to provide a position of the distal end in the patient organ. The device is configured to move along the catheter. The handle includes a control, which is configured to navigate the device along the catheter to a target location in the patient organ. The processor is configured to estimate, based on a location of the position sensor, a target position of the control on the handle that corresponds to the target location of the device, and to set a marker to mark the target position of the control on the handle.

The present invention will be more fully understood from the following detailed description of the embodiments thereof, taken together with the drawings in which:

DETAILED DESCRIPTION OF EMBODIMENTS

Overview

Figure 1:
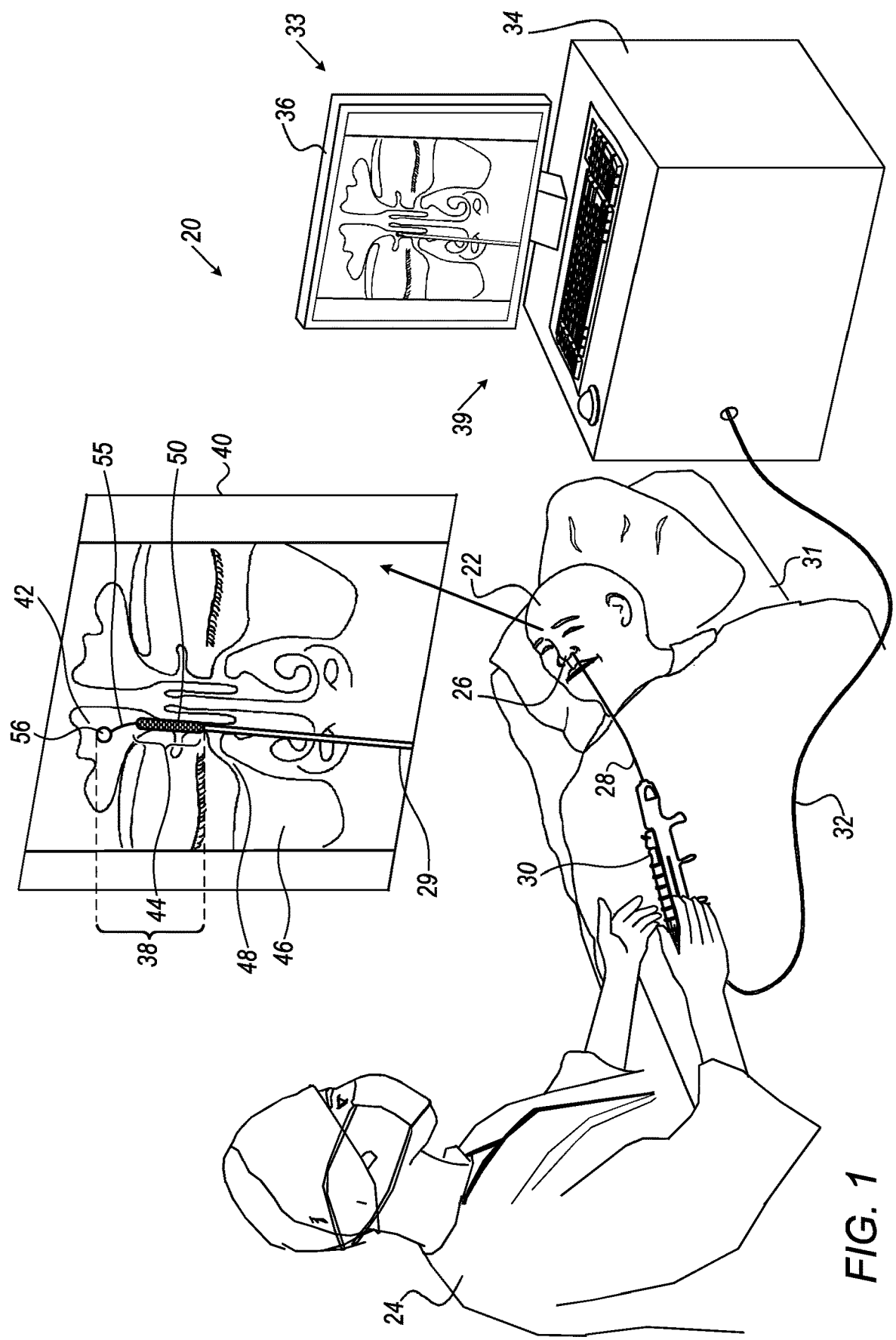
FIG. 1 is a schematic, pictorial illustration of a sinuplasty surgical system, in accordance with an embodiment of the present invention.

Balloon catheters may be used in various medical procedures, for example in treating ear-nose-throat (ENT) diseases such as sinusitis. In sinuplasty procedures that are used for treating sinusitis by inserting a catheter with an inflatable balloon into the ENT system, it is important to accurately position the balloon in the ostium of the sinus.

During navigation of the catheter within the ENT system, a physician may not have direct view or internal imaging of the sinus, and may therefore be unable to see the actual position of the balloon in the ENT system. In such cases, the physician may position and inflate the balloon at a wrong location, e.g., partially or fully out of the sinus ostium, and may have to deflate the balloon and re-attempt the navigation until the balloon is properly positioned. Unintended application of more than a single navigation cycle prolongs the procedure, causes unnecessary pain, and may cause damage to the ENT system of the patient.

Embodiments of the present invention that are described hereinbelow provide improved techniques for accurate positioning of a balloon in the sinus ostium, or in any other target location in the ENT system of the patient. The disclosed methods and systems may be used in various minimally invasive procedures that require accurate positioning of a balloon. The disclosed techniques can be implemented in various types of medical devices, and used in any suitable catheterization procedure that uses an inflatable balloon. The disclosed techniques can more generally be used for accurate positioning of other devices that are inserted into a patient body.

In some embodiments, during procedure planning and before inserting the catheter, the physician acquires one or more anatomical images of the ENT system of the patient. The physician then inserts the catheter into the ENT system, for example through the nose. In some embodiments, the catheterization system comprises a catheter, a position tracking system, which is configured to track the position of the distal end of the catheter in the patient body, and an operating console comprising a processor.

In an embodiment, the catheter comprises a guidewire along which an inflatable balloon can be positioned, and a position sensor attached to the tip of the guidewire. The catheter further comprises a handle comprising controls for navigating the guidewire and the balloon. The physician navigates the distal end of the guidewire to the target location of the balloon, while the processor tracks the position of the tip by registering between the anatomical image and the position sensor. After positioning the distal tip at the target location, the processor uses the tracked location of the position sensor to estimate the setting of the relevant control of the handle that will bring the balloon to the target location.

In some embodiments, the processor displays the estimated location to the physician, who sets a marker on the handle. The marker may comprise, for example, an adjustable mechanical stopper that stops the balloon control on the handle at the appropriate location.

The physician navigates the balloon to the target location by setting the balloon control to the marker/stopper and carries out the sinuplasty procedure (e.g., inflating the balloon to anchor the distal end of the catheter and treating the sinusitis).

The proposed techniques enable the physician to accurately position the balloon, or any other suitable medical device, in the target location in a single attempt, thus reducing unnecessary pain, avoiding potential damage to the patient and shortening the sinuplasty procedure.

System Description

FIG. 1 is a schematic pictorial illustration of a sinuplasty procedure using a surgical system 20, in accordance with an embodiment of the present invention. System 20 comprises a catheter 28, which a physician 24 inserts into a nose 26 of a patient 22 so as to treat an ear-nose-throat (ENT) disease, such as infection in one or more sinuses of patient 22.

System 20 further comprises a console 33, which comprises a processor 34, typically a general-purpose computer, with suitable front end and interface circuits for receiving signals from catheter 28, via a cable 32, and for controlling other components of system 20 described herein. Console 33 further comprises input devices 39 and a display 36, which is configured to display data (e.g., images) received from processor 34 or inputs inserted by a user (e.g., physician 24).

Reference is now made to an inset 40 that shows a frontal anatomical view of the ENT system of patient 22. The ENT system comprises a frontal sinus 42 and a maxillary sinus 46. Ostia 44 and 48 connect between cavities of the nose (not shown) and sinuses 42 and 46, respectively. Catheter 28 comprises a guidewire 29 having a distal end 38. In an embodiment, the tip of distal end 38 comprises a position sensor 56 attached at the end of a residual end section 55 of guidewire 29. Catheter 28 further comprises an inflatable balloon 50, which may be configured in two positions, e.g., an expanded (inflated) position and a collapsed position. When Balloon 50 is in the collapsed position, the catheter can be navigated to the target location. The balloon is then inflated to the expanded position using a suitable fluid (e.g., a saline solution so as to anchor catheter 28 at the target location (e.g., ostium 44) in the ENT system of patient 22.

Catheter 28 further comprises a handle 30, which is located at the proximal end of catheter 28. Handle 30 is configured to control the navigation of guidewire 29 and the motion of balloon 50 along guidewire 29. Handle 30 is described in details in FIG. 2 below.

In an embodiment, the position of position sensor 56 is typically measured by magnetic position sensing in catheter tracking system comprised in system 20. In this case, console comprises a driver circuit (not shown), which drives magnetic field generators (not shown) placed at known positions external to patient 22 lying on table 31, e.g., below the patient's head.

This method of position sensing is implemented in various medical applications, for example, in the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication No. WO 96/05768, and in U.S. Patent Application Publications Nos. 2002/0065455, now U.S. Pat. No. 6,690,963, issued on Feb. 10, 2004, 2003/0120150, now U.S. Pat. No. 7,729,742, issued on Jun. 1, 2010, and 2004/0068178, now abandoned, whose disclosures are all incorporated herein by reference.

During the sinuplasty procedure, physician 24 navigates the tip of guidewire 29 into sinus 42. In some cases, e.g., when treating infection in the sinus, it is important for the physician to anchor the distal tip of the catheter, for example by inflating balloon 50 in ostium 44. In an embodiment, balloon 50 may be 16 mm long and may have a diameter of 5 mm, such as sinuplasty balloon produced by Acclarent Inc. (catalog number RSP0516MFS), yet any other suitable balloon with other dimensions may be used in the disclosed techniques.

After inserting distal end 38 into the ENT system, physician 36 navigates balloon 50 to ostium 44. Note that, typically, balloon 50 does not comprise a position sensor and is not otherwise imaged on display 36. To perform the treatment safely and efficiently, it is important to position balloon 50 accurately within ostium 44. For example, positioning balloon 50 in the nose cavity, short of ostium 44, may not allow the physician to anchor end section 55 within sinus 42, whereas positioning the balloon within sinus 42, deeper than ostium 44, may disturb the physician in treating the infection therein.

In the example of FIG. 1, balloon 50 is used for anchoring end section 55 within sinus 42. In alternative embodiments, any other suitable device may be positioned using the disclosed techniques, instead of balloon 50. Such a device may comprise, for example, an alternative anchoring device for anchoring the end section or for any other diagnostic or treatment purpose. For example, a balloon may be used for treating cardiac arrhythmia at a pulmonary vein (PV) in a PV isolation procedure. In other applications, a drug dispensing device or a stent may be navigated to a specific location in a human organ, using the techniques described above.

In some embodiments, processor 34 is configured to assist physician 24 to position balloon 50 accurately within ostium 44 as will be described in detail in FIGS. 2 and 3 below. FIG. 1 shows only elements related to the disclosed techniques, for the sake of simplicity and clarity. System 20 typically comprises additional modules and elements that are not directly related to the disclosed techniques, and thus, intentionally omitted from FIG. 1 and from the corresponding description.

Processor 34 may be programmed in software to carry out the functions that are used by the system, and to store data in a memory (not shown) to be processed or otherwise used by the software. The software may be downloaded to the processor in electronic form, over a network, for example, or it may be provided on non-transitory tangible media, such as optical, magnetic or electronic memory media. Alternatively, some or all of the functions of processor 34 may be carried out by dedicated or programmable digital hardware components.

Figure 2:
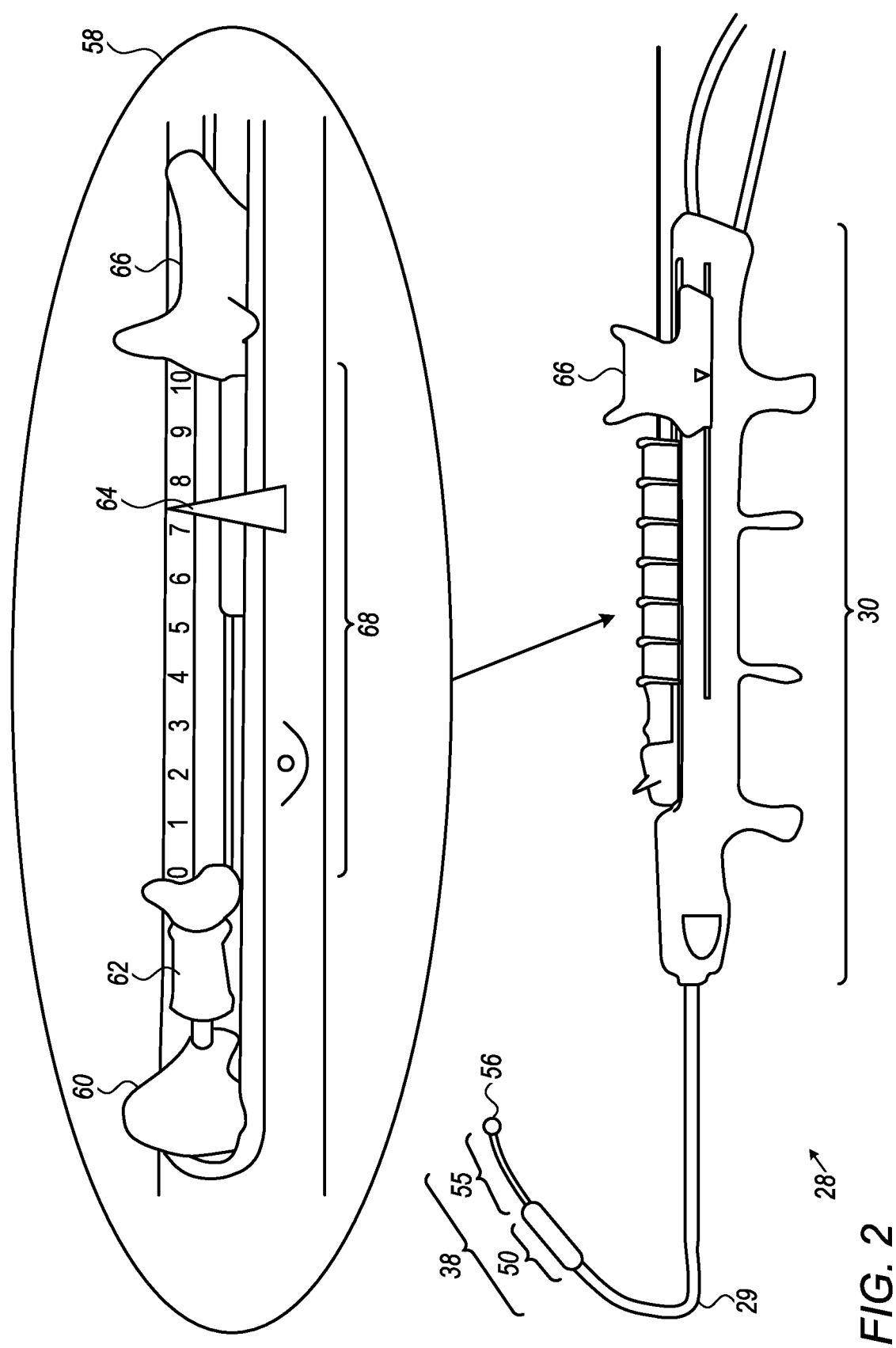
FIG. 2 is a schematic, pictorial illustration of a sinuplasty catheter, in accordance with an embodiment of the present invention.

FIG. 2 is a schematic, pictorial illustration of catheter 28, in accordance with an embodiment of the present invention. Distal end 38 comprises position sensor 56 at the tip of guidewire 29. The length of end section 55 represents the distance between sensor 56 and the position of balloon 50 along the guidewire. In an alternative embodiment, any suitable arrangement of balloon 50 and sensor 56 along guidewire 29 may be used.

In an embodiment, balloon 50 is movable along guidewire 29, but is navigated separately from navigation of the guidewire itself. The length of end section 55 is thus adjustable and controllable by handle 30.

Reference is now made to an inset 58, which is a top-view of handle 30 showing the controls that are used for navigating guidewire 29 and for moving balloon 50 along the guidewire. Handle 30 comprises a wire slider 60, which is configured to slide guidewire 29 into sinus 42, and a wire spinner 62, which is configured to spin distal end 38, for example during the navigation of distal end 38. Handle 30 further comprises a balloon slider 66, which is configured to move balloon 50 along guidewire 29, so as to position the balloon in ostium 44. Physician 24 manipulates wire slider 60, wire spinner 62 and balloon slider 66 as part of the sinuplasty procedure.

In some embodiments, handle 30 comprises a scale 68 and an adjustable marker 64. Marker 64 indicates the position of position slider 66 that brings balloon 50 to its target location in ostium 44. In an embodiment, processor 34 is configured to estimate the correct position of marker 64 on scale 68 and to display the estimated marker position to the physician.

In an embodiment, processor 34 receives the location of the distal end from the position tracking system that tracks position sensor 56. Processor 34 is configured to apply image processing techniques to the CT image to determine the boundaries of sinus 42 so as to set the target location of balloon 50. The processor is further configured to estimate the length of ostium 44 based on the CT image, and by additionally considering the predefined length of balloon 50 to estimate the position of marker 64 on scale 68.

Processor 34 is further configured to display the estimated position of adjustable marker 64 on scale 68, which corresponds to the target location of balloon 50 in ostium 44. In the example of inset 58, physician 24 may position balloon 50 at the target location (e.g., ostium 44) by sliding balloon slider 66 forward about 2.5 cm, until hitting the position of marker 64 at number 7.5 on scale 68. Using this technique, the physician is able to position balloon 50 with high accuracy, even though the balloon does not comprise a position sensor and is not otherwise imaged on display 36.

In some embodiments, marker 64 may be a mechanical stopper, which an operator (e.g., physician 24) sets manually based on an input from processor 34 on display 36. In alternative embodiments, marker 64 is implemented as an optical display on scale 68. In yet alternative embodiments, scale 68 and marker 64 may be implemented as a digital scale and a digital marker, respectively, so that processor 34 may display marker 64 directly on scale 68. Processor 34 may further provide physician 24 with an indication when slider 66 hits the position of marker 64. In some embodiments, marker 64 is implicit, e.g., it may comprise only an indication of the value on scale 68 at which slider 66 is to be positioned. Further alternatively, any other suitable marking apparatus formed in software and/or hardware can also be used.

The configuration of handle 30 and its various controls, as shown in FIG. 2, is an example configuration that is chosen purely for the sake of conceptual clarity. In alternative embodiments, the disclosed techniques can be used with any other suitable handle configuration. For example, the position of balloon 50 may be controlled using any other suitable type of control, not necessarily using a linear slider such as slider 66. For example, the position of balloon 50 may be controlled by a rotary dial or knob. The shape of scale 68 and the positioning of marker 64 are typically determined by the shape and range of motion of the balloon control.

Figure 3:
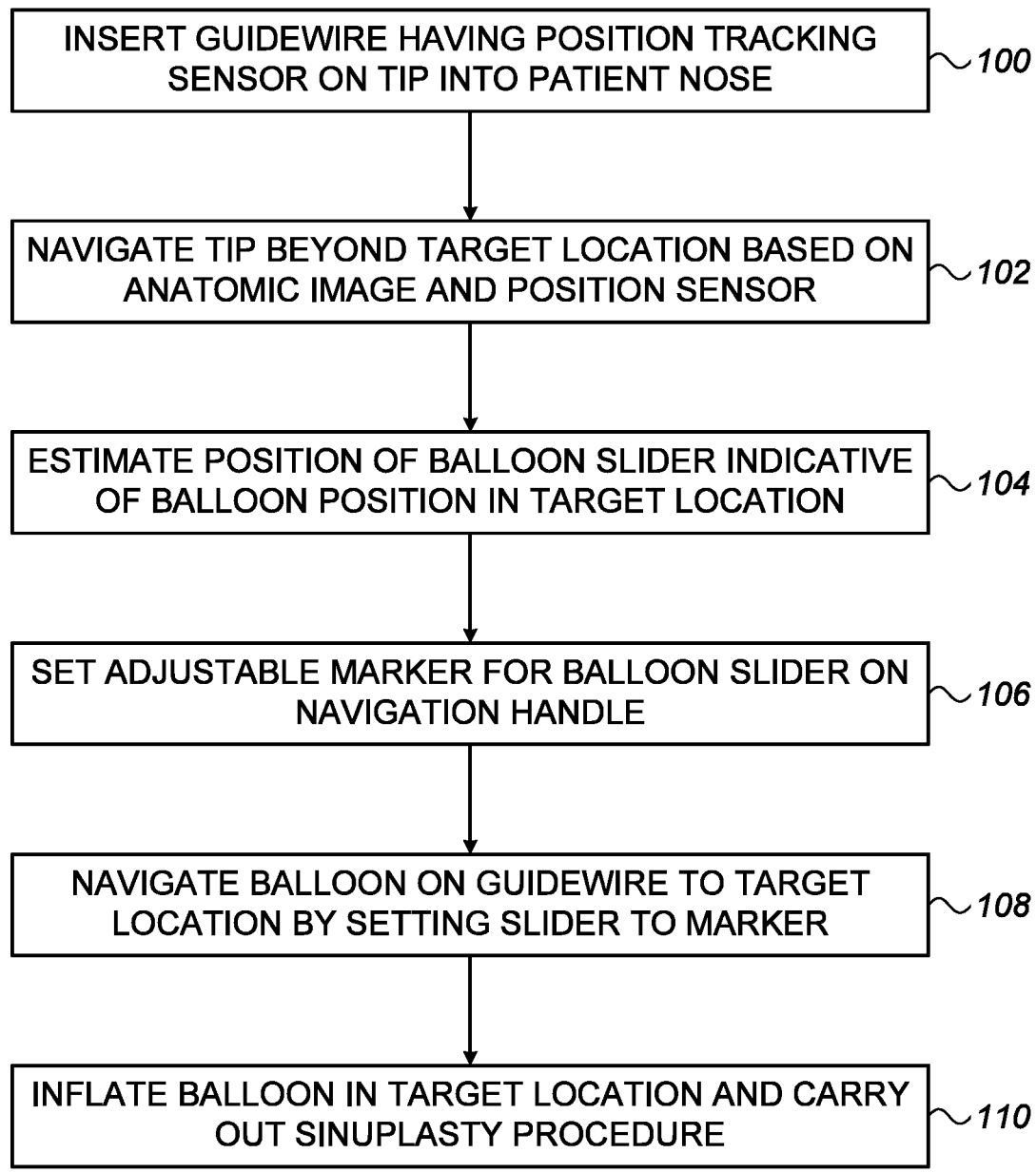
FIG. 3 is a flow chart that schematically illustrates a method for positioning a balloon in a sinus opening, in accordance with an embodiment of the present invention.

FIG. 3 is a flow chart that schematically illustrates a method for positioning balloon 50 in ostium 44, in accordance with an embodiment of the present invention. The method begins with physician 24 inserting guidewire 29 of catheter 28 (as described in FIG. 2) into nose 26 of patient 22, at an insertion step 100.

In an embodiment, before starting the sinuplasty procedure, physician 24 may acquire an anatomical image of the head of patient 22, as shown for example in inset 40 of FIG. 1. The anatomical image may be obtained using any suitable medical imaging technique, such as computerized tomography (CT).

At a tip navigation step 102, physician 24 navigates end section 55 into sinus 42. In some embodiments, physician 24 uses wire slider 60 to slide the guidewire, and wire spinner to rotate the guidewire. Catheter 28 is configured to anchor end section 55 by inflating balloon 50 at the target location, e.g., ostium 44. Sinus 42, in which physician 24 conducts the procedure (e.g., treating sinusitis or any other ENT disease) is located deeper in the ENT system than ostium 44. Therefore, physician 24 navigates position sensor 56, which is typically attached to the distal tip of section 55, into sinus 42, deeper than ostium 44.

In an alternative embodiment, the position sensor may be attached to the intended location of the balloon along the guidewire, in which case physician 24 may navigate the position sensor to ostium 44 instead of into sinus 42.

At a position estimation step 104, processor 34 receives the location of position sensor 56, the CT image and the length of balloon 50, and estimates, based on these inputs, the position of marker 64 on scale 68. The position of marker 64 corresponds to the balloon position along the guidewire and therefore also in ostium 44.

At a marker setting step 106, physician 24 may receive (e.g., as text in display 36) the marker position estimation from processor 36 and adjust marker 64 manually, for example as a mechanical stopper, on scale 68, as described above. In an alternative embodiment, processor 34 may automatically adjust marker 64, for example as an optical display on scale 68.

At a balloon navigation step 108, physician 24 navigates balloon 50 along guidewire 29 to the target location in ostium 44 by moving balloon slider 66 to the position indicated by marker 64 on scale 68. This navigation method is "blind" in a sense that the physician cannot see the actual location of balloon 50 but depends on the marker position estimation by processor 34, as described above. In an embodiment, after positioning balloon 50 in the target location of ostium 44, physician 24 may acquire an additional anatomical image (e.g., using fluoroscopy) to verify that balloon 50 is properly positioned in ostium 44. The disclosed techniques reduce the need for this verification, thereby saving fluoroscopy resources, redundant irradiation to patient 22 and reducing the overall cycle time of the sinuplasty procedure.

At a balloon inflation step 110, physician 24 inflates balloon 50 in ostium 44 so as to anchor distal end 38 and to carry out the sinuplasty procedure.

Although the embodiments described herein mainly address anchoring a catheter distal end in sinuplasty procedures, the methods and systems described herein can also be used in other applications, such as in Electrophysiology (EP) and interventional cardiology or any other catheterization procedure guiding a suitable medical device to a selected location in the patient's body.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
   (a) inserting into an anatomical structure of a patient a catheter comprising:
      (i) a position sensor attached to a distal end of the catheter;
      (ii) a device, which is movable along the catheter; and
      (iii) a handle, comprising a control for navigating the device along the catheter to a target location in the anatomical structure of the patient;
   (b) estimating, based on a location of the position sensor, a target position of the control on the handle that corresponds to the target location of the device;
   (c) setting a marker to mark the target position of the control on the handle without moving the device; and
   (d) after setting the marker, navigating the device to the target location by setting the control to the marker.

2. The method according to claim 1, wherein the anatomical structure is within a head of the patient.

3. The method according to claim 1, wherein the anatomical structure is a frontal recess.

4. The method according to claim 1, wherein the target location is a sinus ostium.

5. The method according to claim 1, further comprising acquiring an anatomical image of the anatomical structure of the patient before inserting the catheter; and registering the location of the position sensor with the anatomical image.

6. The method according to claim 5, wherein estimating the target position comprises determining allowed boundaries for the target location relative to the anatomical image, and estimating the target position based on: the location of the position sensor on the anatomical image; the allowed boundaries; and predefined dimensions of the device.

7. The method according to claim 1, wherein the marker comprises an adjustable mechanical stopper that is configured to move relative to both the handle and the control, wherein setting the marker comprises adjusting a position of the mechanical stopper to the target position on the handle, and wherein setting the control comprises sliding the control on the handle until the control physically hits the mechanical stopper.

8. The method according to claim 1, wherein the device comprises an anchoring device for anchoring the distal end of the catheter in the patient.

9. The method according to claim 8, wherein the anchoring device comprises an inflatable balloon.

10. The method according to claim 1, wherein the marker is a user adjustable marker that is configured to indicate the position of the device that brings the device to the target location in an ostium of the anatomical structure of the patient.

11. A system, comprising:
   (a) a catheter, comprising:
      (i) an insertion tube for insertion into an anatomical structure of a patient;
      (ii) a position sensor attached to a distal end of the catheter, wherein the position sensor is configured to provide a position of the distal end in the anatomical structure of the patient;
      (iii) a device, which is configured to move along the catheter; and
      (iv) a handle comprising a control, wherein the control is configured to move along the handle to navigate the device along the catheter to a target location in the anatomical structure of the patient;
      (v) a marker configured to mark a target position of the control on the handle, wherein the marker is configured to selectively move longitudinally along the handle and relative to the control until the marker abuts the control; and
   (b) a processor, which is configured to:
      (i) estimate, based on a location of the position sensor, the target position of the control on the handle that corresponds to the target location of the device; and
      (ii) set the marker on the handle without moving the device.

12. The system according to claim 11, wherein the anatomical structure is within a head of the patient.

13. The system according to claim 11, wherein the anatomical structure is the frontal recess.

14. The system according to claim 11, wherein the target location is a sinus ostium.

15. The system according to claim 11, wherein the device comprises an inflatable balloon for anchoring the distal end of the catheter in the patient, wherein the system includes a display in signal communication with the processor, wherein the inflatable balloon does not comprise a position sensor and is not imaged on the display.

16. A method, comprising:
(a) inserting into an anatomical structure of a patient a catheter comprising:
   (i) a guidewire, wherein the guidewire is configured to selectively longitudinally advance and selectively rotate,
   (ii) a position sensor attached to a distal end of the guidewire;
   (iii) an inflatable balloon, which is movable along the guidewire, wherein a distal end of the inflatable balloon is positioned proximal to the position sensor; and
   (iv) a handle, comprising a control for navigating the inflatable balloon along the guidewire to a target location in the anatomical structure of the patient;
(b) selectively longitudinally advancing and selectively rotating the guidewire to the target location in the anatomical structure of the patient;
(c) estimating, based on a location of the position sensor, a target position of the control on the handle that corresponds to the target location of the inflatable balloon;
(d) setting a marker on the handle to mark the target position of the control on the handle;
(e) distally advancing the inflatable balloon along the guidewire to the target location by setting the control to the marker; and
(f) inflating the inflatable balloon at the target location in the anatomical structure of the patient.

17. The method according to claim 16, wherein the anatomical structure is in a head of the patient.

18. The method according to claim 16, wherein the anatomical structure is the frontal recess.

19. The method according to claim 16, wherein the target location is a sinus ostium.

20. The method according to claim 16, wherein the handle further comprises a wire spinner, wherein selectively rotating the guidewire further comprises selectively rotating the guidewire using the wire spinner.

* * * * *